United States Patent
Golesworthy et al.

(10) Patent No.: US 8,252,039 B2
(45) Date of Patent: Aug. 28, 2012

(54) AORTIC ROOT DISSECTION TREATMENT

(76) Inventors: Taliesin John Golesworthy, Gloucestershire (GB); Micheal Ulrich Lamperth, Surrey (GB)

(*) Notice: Subject to any disclaimer, the term of this patent is extended or adjusted under 35 U.S.C. 154(b) by 448 days.

(21) Appl. No.: 12/482,080

(22) Filed: Jun. 10, 2009

(65) Prior Publication Data
US 2009/0248138 A1  Oct. 1, 2009

Related U.S. Application Data

(62) Division of application No. 10/527,498, filed as application No. PCT/GB03/04135 on Sep. 18, 2003, now abandoned.

(30) Foreign Application Priority Data

Sep. 19, 2002 (GB) .................................. 0221781.8
Apr. 14, 2003 (GB) .................................. 0308517.2

(51) Int. Cl.
*A61F 2/06* (2006.01)
(52) U.S. Cl. .................................................. 623/1.13
(58) Field of Classification Search ........... 623/1.1, 623/1.12, 1.13, 1.15, 1.19, 1.22, 1.3, 1.31, 623/1.32, 1.34, 1.36, 1.42, 1.44, 11.11
See application file for complete search history.

(56) References Cited

U.S. PATENT DOCUMENTS

| | | | |
|---|---|---|---|
| 3,626,947 A | 12/1971 | Sparks | |
| 4,904,254 A | 2/1990 | Lane | |
| 5,246,456 A | 9/1993 | Wilkinson | |
| 5,476,471 A | 12/1995 | Shifrin et al. | |
| 5,741,215 A | 4/1998 | D'Urso | |
| 6,112,109 A * | 8/2000 | D'Urso | 600/407 |
| 6,165,193 A | 12/2000 | Greene, Jr. et al. | |
| 6,197,050 B1 | 3/2001 | Eno et al. | |
| 6,436,132 B1 * | 8/2002 | Patel et al. | 623/1.13 |
| 6,554,856 B1 | 4/2003 | Doorly et al. | |
| 6,648,911 B1 * | 11/2003 | Sirhan et al. | 623/1.15 |
| 6,899,728 B1 | 5/2005 | Phillips et al. | |
| 7,073,456 B2 | 7/2006 | Phillips et al. | |
| 7,290,494 B2 | 11/2007 | Phillips et al. | |
| 2002/0068968 A1 | 6/2002 | Hupp | |
| 2002/0103527 A1 | 8/2002 | Kocur et al. | |
| 2006/0036311 A1 | 2/2006 | Nakayama et al. | |
| 2006/0129228 A1 | 6/2006 | Golesworthy et al. | |

FOREIGN PATENT DOCUMENTS

| | | |
|---|---|---|
| EP | 1055401 A1 | 11/2000 |
| GB | 2090143 A | 7/1982 |
| GB | 2344053 A | 5/2000 |
| WO | 9740755 A1 | 11/1997 |
| WO | 0239906 A2 | 5/2002 |

* cited by examiner

*Primary Examiner* — Tuan V Nguyen
(74) *Attorney, Agent, or Firm* — Porzio, Bromberg & Newman, P.C.

(57) ABSTRACT

A stent is provided for external application to an artery in which an aneurysm has occurred or is about to occur to provide support thereto, the stent being of bespoke character by virtue of its creation to conform morphologically to the actual contour of the artery captured using for example MRI, CAD and RP.

12 Claims, 6 Drawing Sheets

AORTIC ROOT DISSECTION TREATMENT

This application is a divisional of U.S. patent application Ser. No. 10/527,498 filed Oct. 11, 2005, which is abandoned, which is a National Stage of International Application PCT/GB2003/004135, filed 18 Sep. 2003, which claims the benefit of Application No. 0221781.8, filed in GB on 19 Sep. 2002 and Application No. 0308517.2 filed in GB on 14 Apr. 2003, the disclosures of which Applications are incorporated by reference herein.

This invention concerns improvements in or relating to stents for use in humans.

The present invention has particular but not exclusive reference to a stent for use in association with the ascending aorta.

Aortic dissection is or can be a fatal occurrence since the rupture of the artery occasions dramatic haemorrhaging resulting in system failure. One particular condition afflicting a significant number of people is that known as Marfan's Syndrome which affects the connective tissue in the body to the extent that the aortic root becomes a focus for weakening in time with the pulsing of the blood flow from the heart. The tissue of which the artery is made is weakened and accordingly stretches with a concomitant increase in the diameter of the artery giving rise to dissection or aneurysm. The wall of the artery becomes thinner in section and should distension increase further rupture will occur with the results indicated Supra. In addition, the aortic valve is formed at the base of the aorta and the distension thereof additionally and adversely affects the operational efficiency of the valve with leakage occurring.

Of course, aortic root dissection is not confined to sufferers of Marfan's Syndrome and can affect any one.

Conventionally the surgical procedures for addressing the problem, either electively or on an emergency basis, involve the insertion of a stent in the aorta or the removal of the aortic root and its replacement with a stent incorporating a mechanical valve, or in some cases a pig's valve, the stent being sutured in place. In an alternative procedure the stent is inserted within the aortic root, following appropriate incision thereof, which is then sutured back into position. These procedures do, however, involve considerable expenditure in both time and cost. The deployment of a heart/lung bypass machine is required with all the dangers of infection associated with such intrusive procedures. Post-operatively because of the intimate contact between the blood and the now installed internal replacement root and valve combination a continuing risk of infection remains without limit as to time. Patients having undergone such surgery have to be continuously mindful of the need to secure antibiotic protection whenever potentially intrusive activity on the body is contemplate, for example dentistry. Furthermore due to the increased risk of clotting following surgery of this kind anti-coagulants have to be administered usually on a daily basis with blood tests to check the INR being necessary regularly, thus adding to the on-going cost of patient care.

The conventional stents deployed internally are generally produced from synthetic material one example of which is that available under the trade name DACRON®, a polyester with tough elastic properties. In some designs of internal stent reinforcement giving a degree of rigidity coupled with flexibility is provided and may take the form of a spirally wound open-coiled or mesh insert. The flexibility is necessary to accommodate differing tortuosity of arteries, but the rigidity is also required to resist deformation by kinking for example.

Conventional internal stents for treating aneurysms are available in a range of sizes to fit as appropriate. However the stents do not mould to the internal contours of the distended artery at the point of the aneurysm. The internal stents locate within the artery either side of the aneurysm and accordingly pockets may be formed externally of the stent but within the artery and these pockets may contain blood. In the case of aortic root replacement by removal of the root and substitution with a stent and valve, the diameter of the stent is chosen to match either the exit aperture in the left ventricle, if the valve is to be replaced, or to the lower section of the artery if the valve is not to be replaced. Accordingly the graft of the stent onto the upper end of the aorta adjacent the aortic arch tends not to be such a good fit.

An object of the present invention is to provide a new and improved stent that obviates the need for procedures of such an intrusive character as are currently required.

A further object of the invention is to provide a method of manufacturing the new and improved stent whereby the resultant stent is of customised form.

According to a first aspect of the present invention there is provided a stent adapted for location exteriorly of a blood vessel, the stent being formed in such manner as to be locatable around and in morphological relationship with the said blood vessel, and means for maintaining the stent in such relationship with the blood vessel.

The stent may include a sleeve that may be in two parts and of generally cylindrical form but may include one or more sections of varying form in order to conform to the morphological requirements in any particular case.

The sleeve is provided with appropriately located recesses or apertures for accommodating other interconnecting blood vessels or structures contiguous with the blood vessel being supported by the stent.

The sleeve of the stent may be provided with a base or flange portion for attachment to a main heart structure, for example the ventricle muscle, such that a securement or anchor point is established for the stent. The base or flange portion may be adapted for appropriate suturing or other means to the said structure. For example the other means may include stapling or adhesion.

In an alternative form of the stent of the present invention the sleeve may not be required to be secured to the heart structure and may be of such morphological size-matching to the blood vessel as to obviate the need for additional securement. In such event the stent effectively moulds to the shape of the blood vessel, e.g. the ascending aorta, and in this manner provides the necessary support and positive location as required. In one embodiment the stent may be tapered at either end in opposite directions such that when in position on the vessel, the stent locks in position and is thus maintained in its appropriate location.

The interconnection of the parts of the sleeve may be effected by a hinge mechanism with releasable latches provided at the mating edges of the parts.

In the alternative, the sleeve may be of resilient material slit longitudinally to allow it to be expanded over the wall of the artery and then to recover its original condition, the sleeve being suitably clampable in position embracing the artery in the said morphological relationship. The clamping may be achieved by the application of suitable ties, for example those known as cable ties which lock firmly around the sleeve, which may be provided with one or more grooves for receiving and locating the ties. The clamping may alternatively be effected by the insertion of a locking pin extendable through hinge elements provided at the mating edges of the slit in the sleeve.

It will be appreciated that other means of securing together the parts of the stent sleeve may be adopted without departing from the present invention. For example zip fasteners appropriately designed to avoid the presence of surfaces that may snag and provided with suitable means for this purpose. In particular the surface of the fastener in contact with the blood vessel, e.g. the aorta, should be of such character as not to give rise to fretting. In this respect a protective flap could be provided.

The sleeve of the stent may be of varying thickness with the greatest thickness being provided in the base or flange region thereof to provide strength at the point of attachment. The thickness may therefore reduce away from that region to afford a degree of flexing given the need to accommodate the pulsing of the blood through the artery.

The sleeve may have an outer casing and a relatively inner casing, the outer casing being of more rigid construction than the inner casing which latter may be configured to provide the flexure mentioned above. In this connection the inner casing may be of petal-like form to encompass the artery but to allow flexing.

In an alternative embodiment the stent of the present invention is formed of one or more parts of spiral formation whereby when in position around the blood vessel close support is given thereto. An advantage of this embodiment lies in its potential for feeding on to the vessel and reforming into a spirally wound coil to provide a unitary support. In position the spiral formation may form either an open coil or a closed coil and may accordingly constitute a former like structure surrounding the blood vessel. This embodiment may be in one or more sections dependent upon the axial length and form required. Suitable interconnections for the sections are provided and may be in the form of screw fitments or their equivalent whereby upon tightening the coil embraces and supports the blood vessel.

The spiral form of stent of the present invention may allow tissue growth within its interstices thereby serving to enhance its integrity in relation to the blood vessel and concomitantly its strength.

The inner surface of the stent must be of a smoothness to ensure that no fretting or abrasion occurs and for similar reasons the external surface of the stent must equally be tolerant of other adjacent body parts, for example other blood vessels or the pericardial wall.

The inner surface of the stent may be suitably contoured or profiled to minimise fretting or abrasion and to assist in the egress of metabolites that may issue from the outer surface of the blood vessel into contact with the stent. The inner surface of the stent may in this even assist in the movement of the metabolites into the pericardial space possibly with a peristaltic effect. Further, the contouring or customising of the stent in this fashion assists in restricting axial movement of the blood vessel, e.g. the aorta, tending thereby to ensure the containment of the vessel within the limits of the stent. The stent thus acts as a mechanical barrier to axial as well as diametral movement of the blood vessel.

The material from which the stent is produced must possess structural integrity in terms of its burst strength, bend strength, tensile strength, liquid porosity, load distribution and general security particularly for mounting to the heart muscle. Further the material should possess a degree of opacity but should be translucent for the purposes of allowing non-intrusive investigative procedures to take place, for example MRI scanning. The material should, however, be resistant to the effect of electromagnetic fields.

The material must also be thermally stable given the potentially variable nature of its working environment and has to be biocompatible in terms of its location within the body structure. In particular, it must possess mechanical, chemical, thermal, proteinal, enzymal and pericardial fluid biocompatibility and resistance to attack from any of these sources.

The material from which the stent may be made may contain antibiotics gradually releasable in time, the antibiotic elements being incorporated during the manufacture of the stent.

The material from which the stent may be made may be polymeric, metallic, or ceramic or appropriate mixtures thereof to meet the requirements of strength and compatibility hereinbefore mentioned. Another material that may be appropriate is a heat shrink plastics material that would be recoverable in terms of shape either immediately or over a period of time to produce the morphological fit, which is an important novel and inventive step of the present invention. The recovery of the plastics material may be in-built such that it occurs over a period of time or in the alternative the recovery could be triggered by appropriate external means.

The material from which the stent may be produced may be polymeric polypropylene, polyester, PTFE or a polyoxymethylene homopolymer such as that available from Du Pont under the name DELRIN®, or a ultra high molecular weight polyethylene. Further, the polymeric material may have applied thereto embroidery of suitable material, for example suture material.

In general the stent of the invention may be of such form as to be adjustable following its initial application to the affected blood vessel. Such adjustment may be capable of initiation externally of the patient's body and may be electronic.

According to a second aspect of the invention there is provided a method of manufacturing a stent according to the first aspect for morphologically fitting an artery including the steps of producing a computerised 3D model from a scanned image of the artery to which the stent is in practice to be applied, and rapid prototyping the computerised 3D model in an appropriate material to provide the stent or a mould for the stent or a precursor therefor.

As indicated supra the material from which the stent may be made may be polymeric and there may be applied thereto a woven or embroidered structure made of for example suture thread. One method of making the morphological form of stent according to the second aspect of the invention is to generate a thin polymeric shell of appropriate form and then to lay down thereon a meshwork of filamentary material to produce a embroidered or textile layer of its own inherent integrity on the surface of the polymeric shell which acts as a former for the stent. Once the embroidery has been completed the polymeric material is removed by suitable means, for example by thermal, chemical or solvent means thus leaving the morphologically shaped stent constituted by the woven structure. In order for the stent to be capable of application to a blood vessel, it would be necessary to incise the stent to allow entry thereinto of the vessel and then to resuture the free edges to provide a complete supporting structure surrounding the vessel.

In a further method of producing the stent of the present invention, again a thin 3-dimensional shell is produced from polymeric material conforming to the morphological profile of the vessel for which the stent is intended. The stent is generated by heat forming, machining, rapid prototyping or similar process and is then mounted in a computer numerically controlled machine having multi-axis control. Appropriate perforations in the shell are then machined in to provide the requisite apertures and other features with the apposite mechanical properties. The machining may be accomplished using one or more of a variety of processes, viz. water jet cutting, laser cutting, drilling or other appropriate machining methods.

A still further method involves the use of a flaccid support which mimics the three-dimensional morphology of the desired form and the application thereto of an embroidered or woven structure using a computer numerically controlled machine incorporating variable support radius. Once the embroidered woven layer is laid down on the flaccid support, the combination may then be used as the finished stent with suitable entry formations for application to the blood vessel. The flaccid support is dissolved away leaving the woven structure for application in the manner indicated.

A further method of producing the stent includes the steps of opening the thorax of the patient, the applying a polymeric wrap by hand to an approximate fit around the blood vessel and thermally treating the wrap to fix it in situ to the shape of the vessel, and closing the thorax.

A still further method of producing the stent includes the steps of opening the thorax and the pericardium, applying shuttering to the blood vessel, injecting room temperature vulcanising (RTV) or room temperature curing polymer around the blood vessel and within the shuttering, allowing the setting of the polymer, removing the shuttering and closing the thorax.

A third aspect of the invention is a stent made in accordance with the method.

The scanned image may be generated for example from an MRI procedure applied to the affected artery of the patient and is then computerised and converted into a stent design. Other investigative procedures may be adopted for the initial imaging step, for example MRA, X-ray CT, 3D pulsed Doppler Echo measuring, namely a 3D version of 2D echocardiography used for aortic root measurement, and any other appropriate imaging technique. Suitable CAD software is employed to create the requisite customised 3D model of the affected artery and this image is then utilised for the rapid prototyping stage. The rapid prototyping, conventionally known in its abbreviated form as 'RP', is conducted on a suitable machine in which is produced in a suitable material a three-dimensional reproduction of the CAD image. The RP reproduction may give the actual stent or may provide the model from which the stent may be produced. In this latter respect, the model may be used to generate a mould from which the stent may be produced, in a similar vein to the 'lost wax' process. In either case the stent so generated is customised for the individual patient and contrasts sharply with the current procedures using internally applied stents of stock sizes.

The RP method may employ Stereo Lithography (SLA), Selective Laser Sintering (SLS) Solid ground curing (SOLIDER) Laminated object manufacturing (LOM) Fused deposition modelling (FDM) or Computer Numerical Controlled (CNC) machining for producing the stent.

The present invention will now be described by way of example only with respect to the accompanying drawings wherein.

Figure 1:
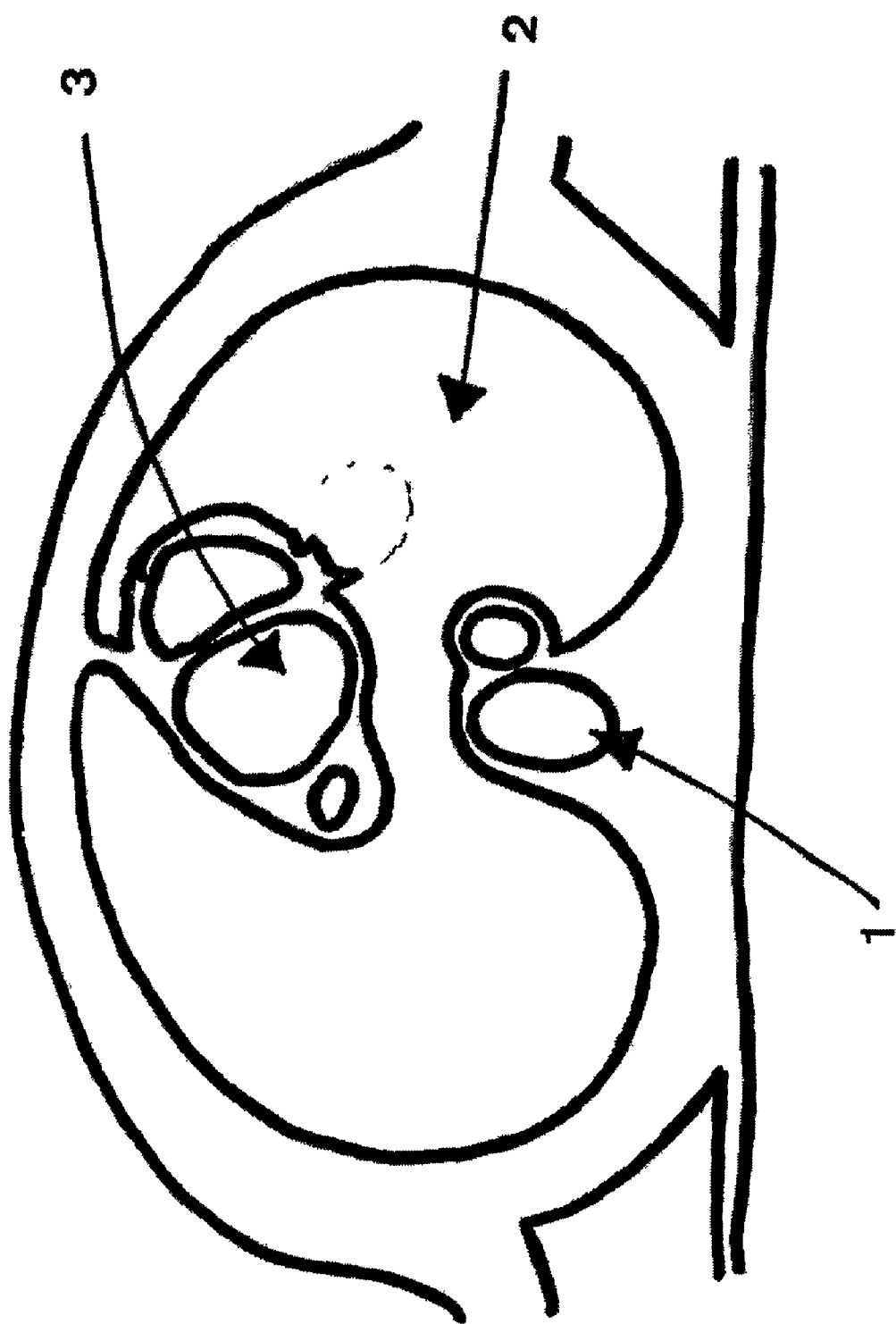
FIG. 1 shows a typical horizontal section through a human thorax clearly indicating the structures of the heart.

In the practice of the present invention the patient is first scanned using a standard medical MRI unit. For example, the scans are taken of the affected structure, e.g. ascending aorta, in such a way as to provide adjacent images substantially axial to the plane of the aorta. Poor quality images may be enhanced by multiple imaging and averaging/superposition of identical images. In some cases it may be appropriate to sedate the patient to improve image quality. FIG. 1 below shows a typical horizontal section through a human thorax clearly indicating the structures of the heart. Reference numeral 1 indicates the spine at the rear of the thorax, 2 indicates the left lung and 3 the structures of the heart.

Figure 2:
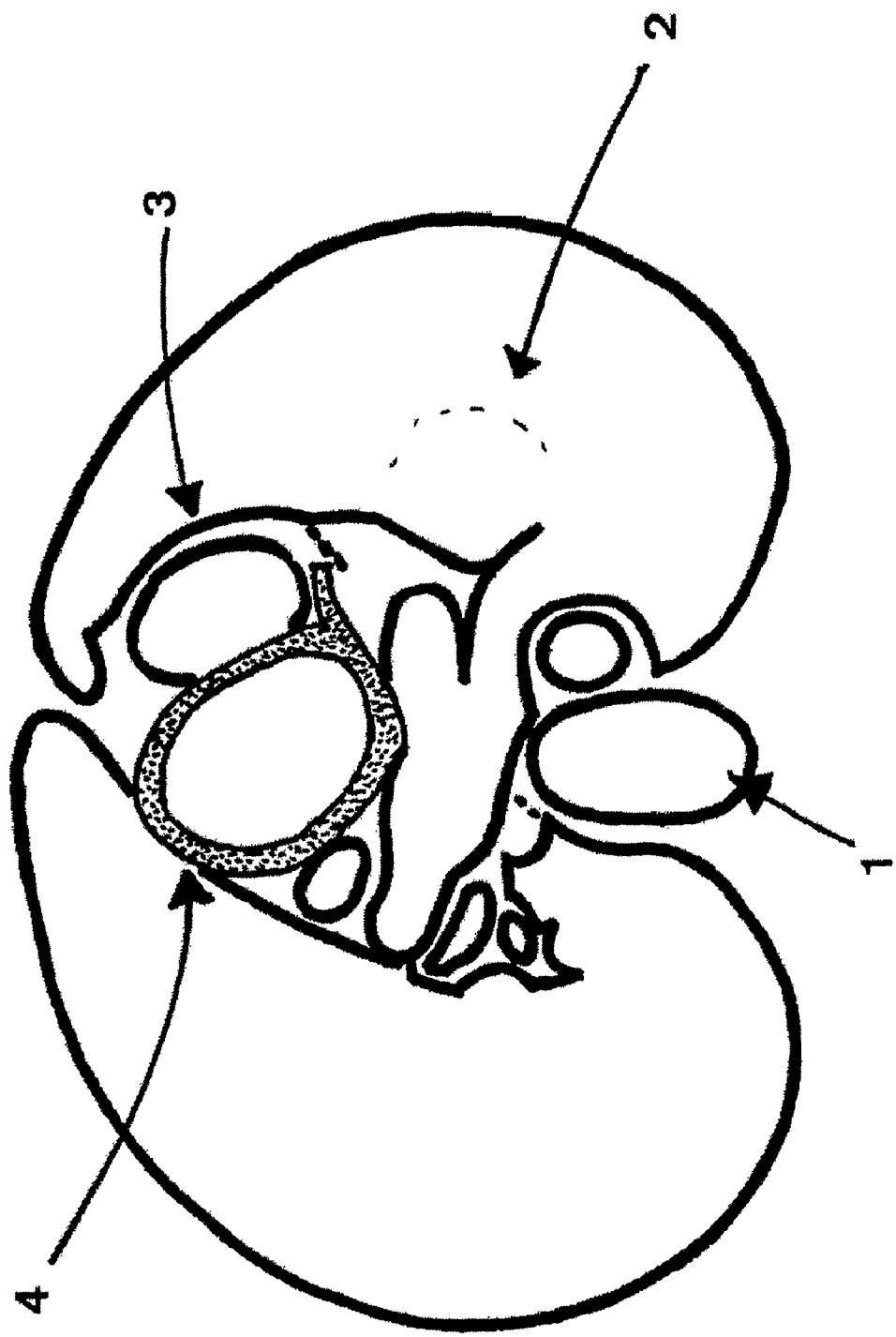
FIG. 2 shows a digitally highlighted horizontal section of the ascending aorta taken from a thoracic MRI image

After the images have been taken, they are transferred to a standard PC computer running appropriate 3-dimensional computer aided design (CAD) software. A number of proprietary CAD packages are available a number of which are suited for the reconstruction of anatomical structures such as the ascending aorta. The MRI thoracic slice images are processed using image analysis software to extract the desired structure, in this case the ascending aorta (from the aortic annulus to the aortic arch). FIG. 2 shows a similar MRI horizontal section through a human thorax including the spine 1, the left lung 2, the heart 3 and a section of the ascending aorta digitally highlighted at 4.

Figure 3:
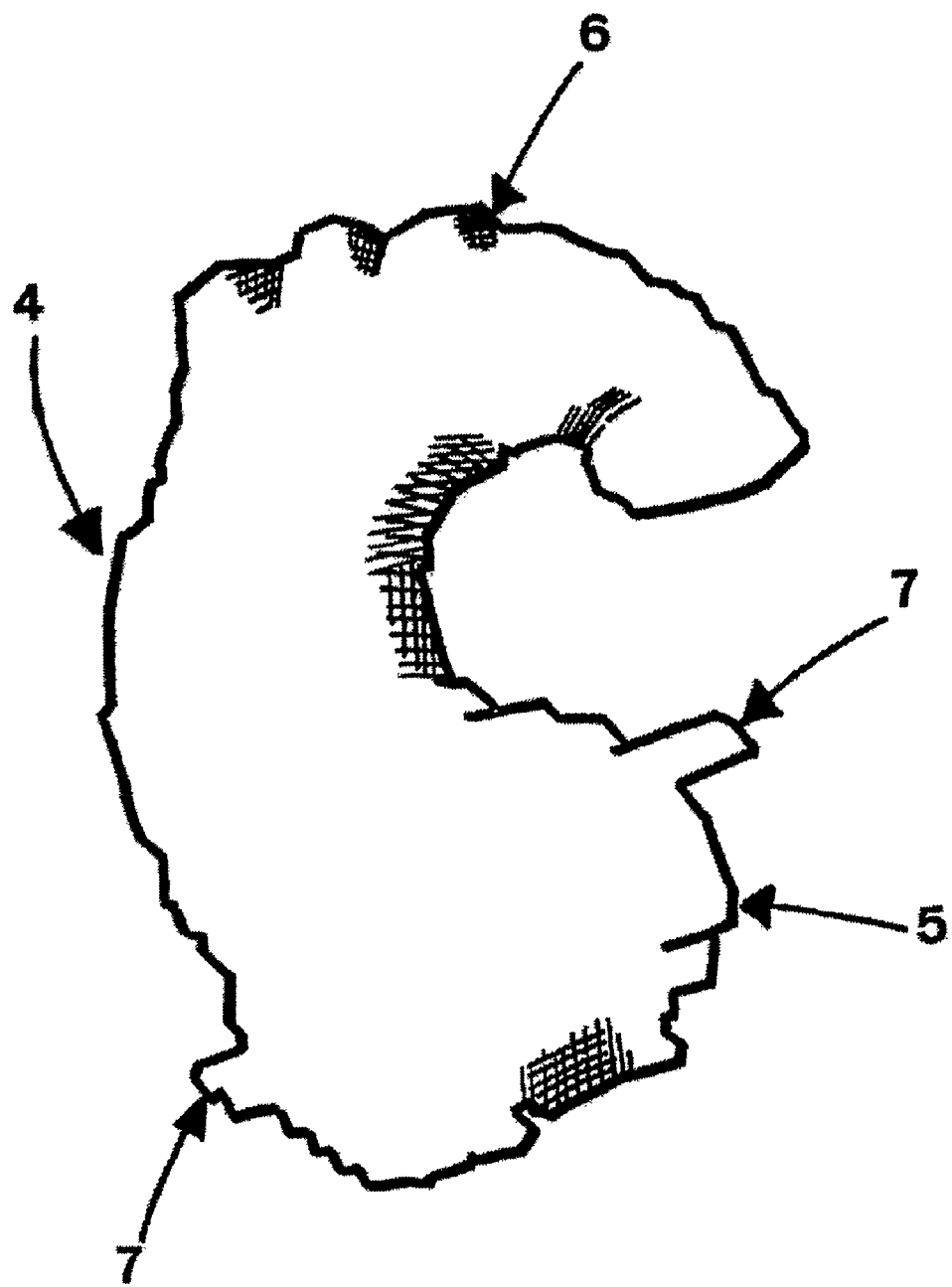
FIG. 3 shows a CAD reconstruction of an ascending aorta and aortic arch.

The aortic slices are then reconstructed within the CAD software using the image data and positional data from the MRI data files. FIG. 3 shows a CAD reconstruction including the ascending aorta 4, the aortic root containing the aortic valve 5, the aortic arch 6 and the coronary artery origins 7.

Figure 4:
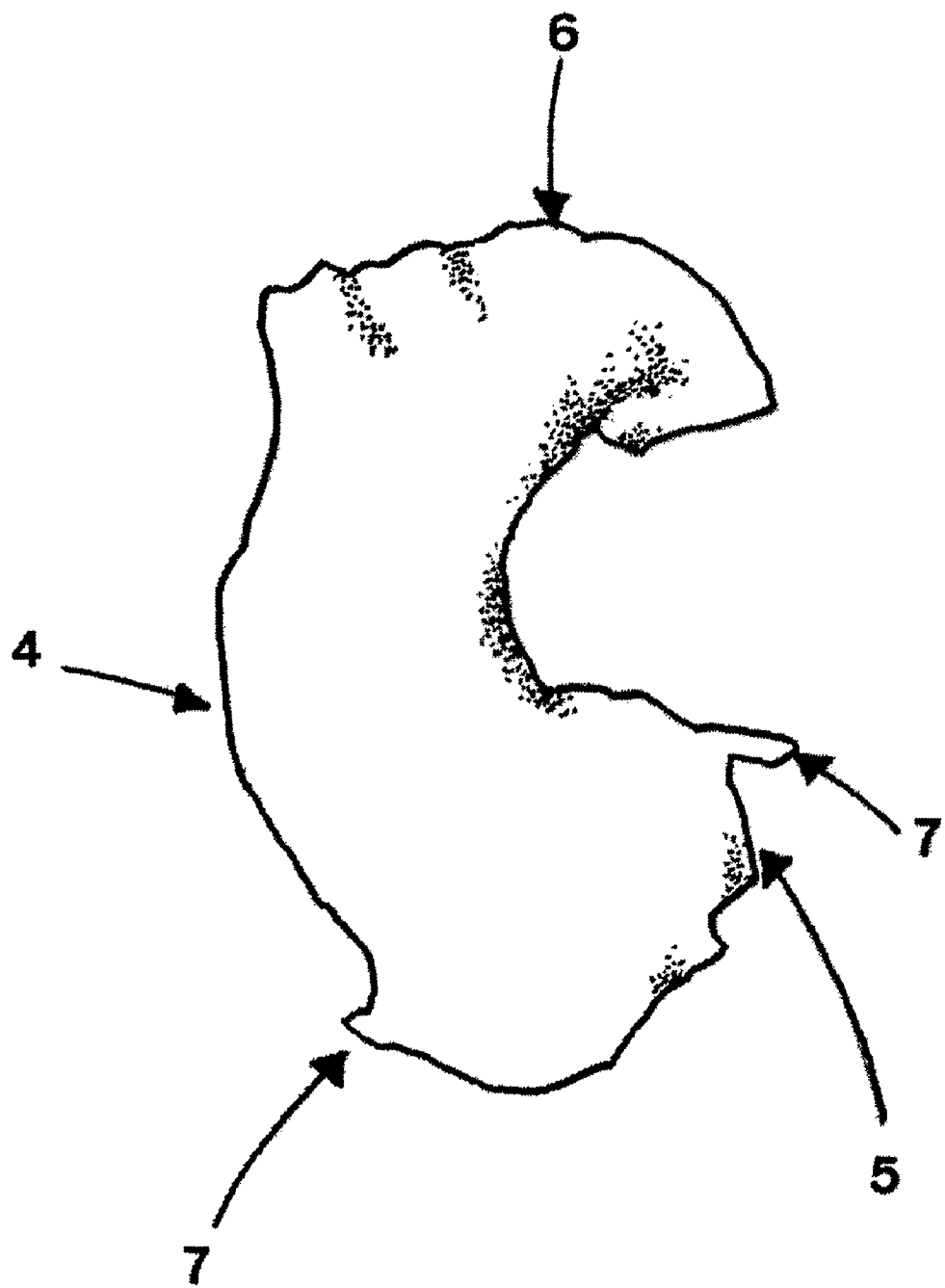
FIG. 4 shows a CAD reconstruction of an ascending aorta and aortic arch post smoothing
Figure 5:
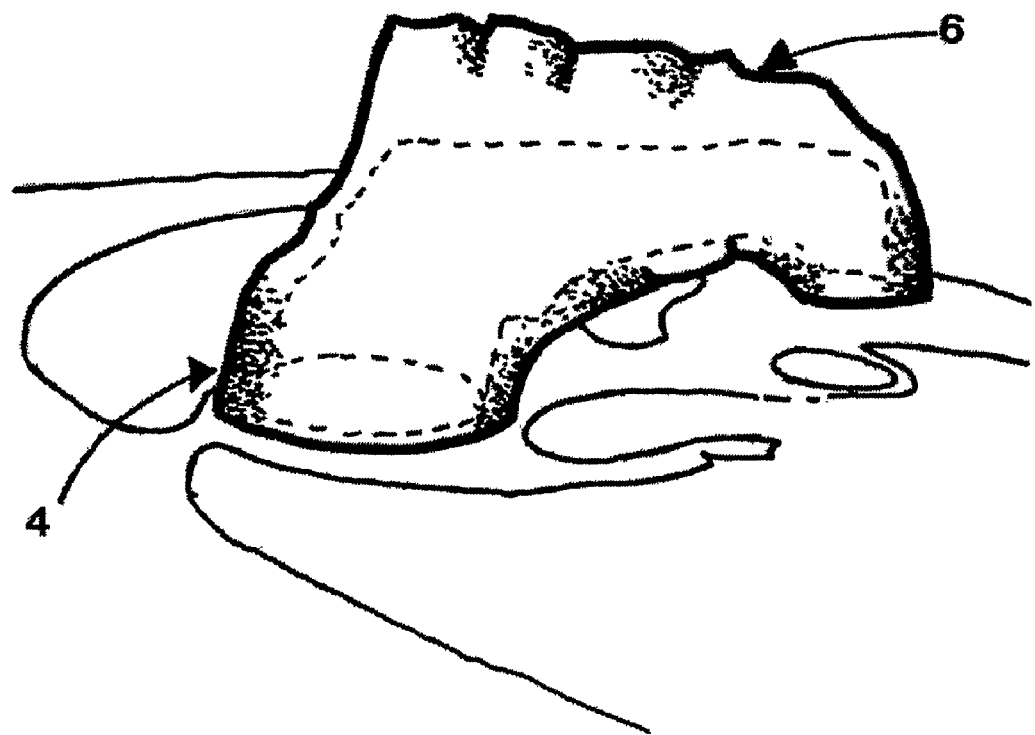
FIG. 5 shows a superimposition of a CAD reconstruction of an ascending aorta with one of the source MRI data files superimposed in the correct spatial position.

Appropriate smoothing algorithms within the CAD software are used to interpolate between successive MRI images to produce a naturally contoured CAD model. Care must be taken, in the case of the ascending aorta, in correctly identifying and positioning the coronary arteries. This process is best done by examination of the MRI images by an appropriately qualified anatomist/surgeon. FIG. 4 shows a CAD model of the same ascending aorta 4, aortic root 5, aortic 6 and coronary origins 7, post smoothing The CAD model can be validated within some CAD packages by superimposition of base MRI image data onto the finished CAD model. FIG. 5 below shows the superimposition of the CAD reconstruction with an MRI image slice from the source data. Structures visible include the upper part of the ascending aorta 4 and the aortic arch 6

The CAD model can then be used to manufacture a tool from which the stent can be manufactured. Depending on the manufacturing method, the physical model can be manufactured as follows: The CAD model file can be transferred to an appropriate Rapid Prototyping machine, e.g. a stereo lithography machine (SLA) to produce a physical model of the ascending aorta in a polymer, e.g. UV curable epoxy resin. This model can then be used to produce a mould in a silicone rubber. The mould can then be used to produce daughter models of the aorta. Other manufacturing techniques can be used, for example selective laser sintering (SLS), CNC machining etc.

Figure 6:
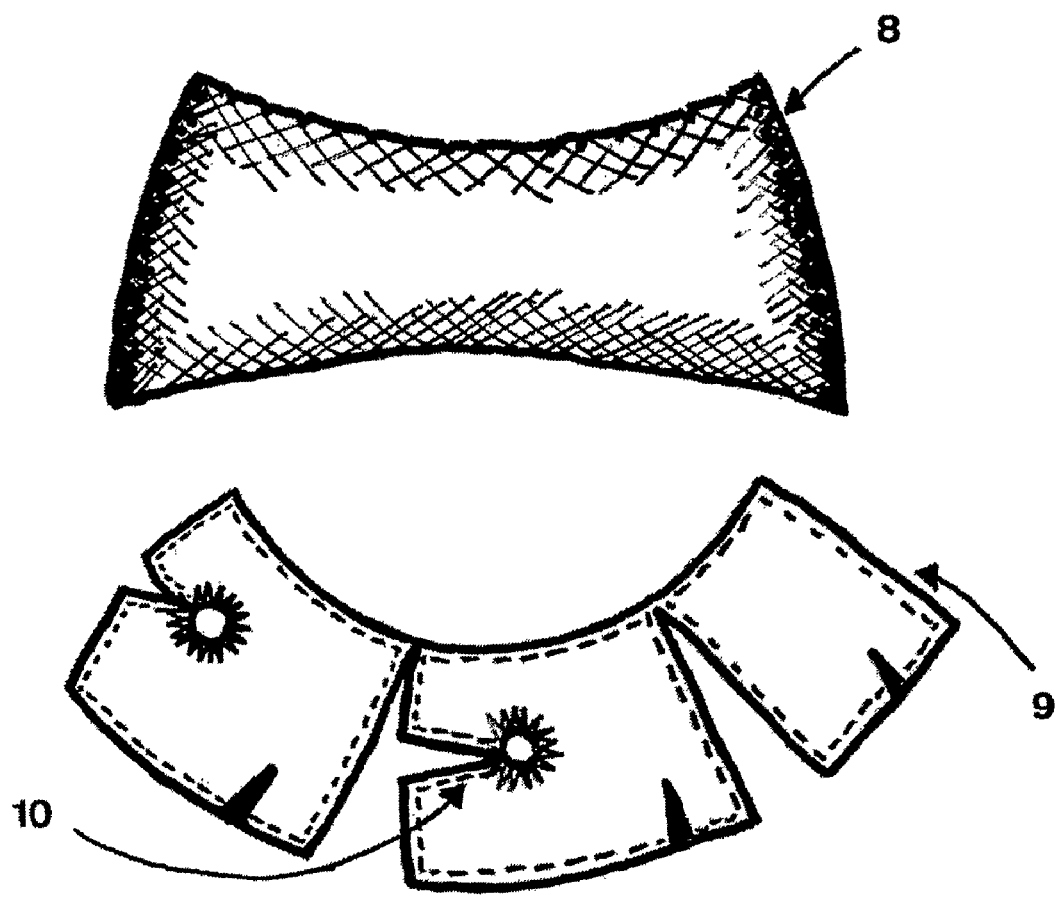
FIG. 6 shows an external support in 2 pieces.

The physical models thus produced are then used in a number of manufacturing processes to produce the finished stent:

1. Embroidering: Linear dimensional data are taken from a 2 dimensional projection of the 3 dimensional CAD reconstruction and used to produce a number of components on a standard computer controlled embroidering machine. The components are embroidered in a medical grade, multi-filament suturing thread, e.g. Polyester to produce an open structured net. The components are embroidered onto a water-soluble polymeric sheet in the CNC embroidering machine. Post-production, the water-soluble sheet is dissolved away and the components are stitched together, assuming their 3 dimensional shape during collocation. The finished stent is then sterilised, for example by steam heating, irradiation etc, prior to packing and transit to the surgeon for implantation. FIG. 6 shows an external stent manufactured in 2 components which, when sutured together assume the 3 dimensional shape. The 2 pieces fit the ascending aorta 8 and the aortic root 9 and include manufactured access within the aortic root section for the coronary origins 10.

2. Heat setting: A medical grade open structure mesh tube of multifilament, heat shrinkable, polymer is obtained of a diameter suitable to fit the largest outside diameter of the structure to be supported. The 3-dimensional CAD reconstruction of the structure is transferred to a Rapid Prototyping machine, e.g. Stereo Lithography (SLA) or Selective Laser Sintering (SLS) and a 3-dimensional physical model is produced in an appropriate polymer, e.g. an epoxide. This model is then used to produce a mould, for example a split mould, in an appropriate material, e.g. silicone rubber. From the mould, a solid pattern is produced. A suitably sized section of the heat shrinkable polymer mesh tube is slipped over the pattern and the two components are placed in a laboratory oven for an appropriate time at an appropriate temperature (to suit the characteristics of the polymer in question). After this exposure, the pattern and polymer mesh are removed from the oven. The polymeric mesh tube has shrunk to conform to the morphology of the pattern to a very high degree of accuracy to form the external stent. The stent is then removed from the pattern, for example by cutting an axial line along the stent in the anterior position with regard to the patient's thorax. The stent is then appropriately sterilised, packaged, and sent to the surgeon for implantation.

3. Vacuum deposition: The 3-dimensional CAD reconstruction of the bodily structure is transferred to a Rapid Prototyping machine from which a 3 dimensional physical model is produced. This model is either gas porous of itself or is used to model a rigid mesh, e.g. metallic mesh, that is gas porous. The gas porous pattern is then mounted in a vacuum deposition manufacturing machine wherein air is drawn through the gas porous pattern within an enclosed chamber. A "cloud" of appropriate polymeric fibres is introduced into the chamber and drawn onto the outside of the gas porous pattern by the airflow through the pattern. When a deposited "felt" of fibres has formed of appropriate thickness, controllable by time and fibre feed rate, and density, controllable by air flow rate through the gas porous pattern, the pattern and its attendant "felt" is transferred to an oven where the fibres are thermally bonded to each other by exposure in said oven for an appropriate time at an appropriate temperature, both being dependent on the selected polymer fibre. When the consolidated felt stent is removed from the oven it is separated from the gas porous pattern, e.g. by collapsing the pattern or cutting the stent, sterilised, packed and sent to the surgeon.

In all cases, surgical implantation is effected by conventional means using existing surgical procedures to reveal the ascending aorta from the aortic annulus to the arch and accommodating the coronary arteries. Said means would include for example surgical sub-procedures taken from the Ross procedure to expose the aortic annulus.

The stent of the invention conforms morphologically to the contours of the affected artery and when applied effectively provides a clamped sleeve to support its exterior in substantially full contact therewith. In the case of an aortic root the clamping of the sleeve also provides an adjustment for the aortic valve in terms of repositioning the valve seat to reinstate or reinforce integrity to prevent leakage at this location, thus avoiding the need to replace the valve.

The present invention does not require the high degree of invasive surgery associated with conventional surgical procedures for aortic root resection and valve replacement. Importantly also when the stent is in place although clearly it is in contact with bodily fluids and internal features of the pericardium and neighbouring parts, its external nature means that it is not in contact with blood. This very facet of the invention is of high benefit in terms of avoiding the possibility of infection affecting the blood stream and also obviates or significantly reduces the dependency of the patient, having undergone the successful procedure, on aftercare and drugs and treatment associated therewith. Quite apart from these advantages the avoidance of such invasive surgery is clearly less traumatic for the patient.

Beating heart surgery thus becomes a possibility by virtue of the present invention, which provides a bespoke stent. Indeed with some forms of the stent, for example the spirally wound version, the opportunity arises for keyhole surgery with all the attendant advantages which that offers in terms of non-intrusive procedures with less patient trauma and post-operative care and medication.

It will be appreciated that whilst the present invention has been described principally with reference to aortic root resection, it has a wider applicability generally to the treatment of aneurysms in any blood vessel and accordingly any reference herein to 'arteries' is to be construed in the wider context of blood vessels generally.

The invention claimed is:

1. A method of treating aortic root dissection in a patient having an ascending aorta in need of such treatment, wherein the ascending aorta has a valve, the method comprises the steps of:
    providing a resilient tubular support sleeve comprising longitudinal mating edges, a proximal part having a proximal part thickness, a distal part having a distal part thickness, and a base or a flange having a thickness greater than the proximal part thickness and the distal part thickness;
    wherein the resilient tubular support sleeve is pre-formed with a size shape that morphologically matches the morphological profile and contour of the ascending aorta;
    locating the resilient tubular support sleeve around the ascending aorta;
    securing the logitudinal mating edges; and
    attaching the base or the flange to ventricle muscle, thereby, reinforces or reinstates valve seat to prevent valve leakage.

2. A method as defined in claim 1 further comprises the steps of:
    (i) forming the resilient tubular support sleeve, wherein the forming step comprising the steps:
        (a) producing a 3D computerised model from a scanned image of the ascending aorta;
        (b) using the 3D computerized model for rapid prototyping the resilient tubular sleeve in an appropriate material to provide the resilient tubular support sleeve or for rapid prototyping a mould for the resilient tubular support sleeve or a precursor thereof.

3. A method as defined in claim 2 wherein the ascending aorta has one or more interconnecting arteries, wherein step (i) further comprises the step of:

forming the resilient tubular support sleeve with appropriately located recesses or apertures for accommodating the one or more interconnecting arteries.

4. A method as defined in claim 2 wherein the resilient tubular support sleeve has varying thickness.

5. A method as defined in claim 2 wherein the thickness of the distal part and proximal part reduces away from the base or the flange to provide flexibility to the resilient tubular sleeve, thereby, accommodating the pulsing of the blood through the ascending aorta.

6. A method as defined in claim 2 wherein step (i) comprises forming the resilient tubular support sleeve from a heat shrink plastics material recoverable in terms of shape either immediately or over a period of time to produce the morphological fit.

7. A method as defined in claim 2 wherein step (a) comprises obtaining the scanned image from a procedure selected from the group consisting of: MRI, MRA, X-ray CT, 3D pulsed Doppler Echo imaging and an equivalent of any one of the foregoing.

8. A method as defined in claim 2 wherein step (a) comprises generating the computerised 3D model using computer-aided design software.

9. A method as defined in claim 2 wherein step (b) comprises employing the computerised 3D model to generate a precursor of the resilient tubular support sleeve, a mould is taken of the precursor, and the resilient tubular support sleeve is then formed using the mould.

10. A method as defined in claim 2 which method further comprises the step of: (c) forming the resilient tubular support sleeve from polymeric material produced to conform morphologically to the 3D image in the form of a thin shell, the shell is mounted in a computer numerically controlled machine having multiple axes control, and the shell is machined to provide appropriate perforations to accommodate subsidiary the ascending aorta.

11. A method as defined in claim 2 wherein step (i) comprises customising the resilient tubular support sleeve for the patient.

12. A method as defined in claim 2 wherein step (i) is carried out before the resilient tubular support sleeve is applied to the ascending aorta.

\* \* \* \* \*